United States Patent
Yang

(10) Patent No.: US 6,926,938 B2
(45) Date of Patent: Aug. 9, 2005

(54) HARDSHELL GELATIN CAPSULE REDUCING THE STATIC ELECTRICITY AND ENHANCING THE LUBRICATION OF FILM

(75) Inventor: Joo Hwan Yang, Kyonggi-do (KR)

(73) Assignee: Suheung Capsule Co., Ltd., Kyounggi-do (KR)

(*) Notice: Subject to any disclaimer, the term of this patent is extended or adjusted under 35 U.S.C. 154(b) by 14 days.

(21) Appl. No.: 10/627,868

(22) Filed: Jul. 28, 2003

(65) Prior Publication Data

US 2004/0018231 A1 Jan. 29, 2004

Related U.S. Application Data

(63) Continuation-in-part of application No. 09/756,708, filed on Jan. 10, 2001, now abandoned.

(51) Int. Cl.$^7$ .............................................. A61K 09/20
(52) U.S. Cl. ..................... 428/35.7; 424/456; 424/460; 424/461; 424/463; 424/465; 424/476; 424/490; 424/498; 424/499

(58) Field of Search .................................. 424/456, 460, 424/461, 463, 465, 476, 490, 498, 499; 428/35.7

(56) References Cited

U.S. PATENT DOCUMENTS

| | | | | |
|---|---|---|---|---|
| 5,869,102 A | * | 2/1999 | Stroppolo et al. | ........... 424/465 |
| 6,309,663 B1 | * | 10/2001 | Patel et al. | ................. 424/450 |
| 6,551,617 B1 | * | 4/2003 | Corbo et al. | ................. 424/465 |

* cited by examiner

*Primary Examiner*—Sandra M. Nolan-Rayford
(74) *Attorney, Agent, or Firm*—Jacobson Holman PLLC

(57) ABSTRACT

The present invention provides a process for preparing hardshell gelatin capsule reducing the static electricity and enhancing the lubrication of film having good film distribution in capsule comprising the steps of: i) preparing an emulsion containing 0.4~0.8 part by weight of diacetylated monoglycerides, 0.05~0.1 part by weight of sodium lauryl sulfate, and 0.005~0.01 part by weight of colloidal silicon dioxide; ii) adding the emulsion to gelatin solution containing 100 part by weight of gelatin; iii) mixing and homogenizing the resulting solution; iv) adjusting viscosity of mixture; v) allowing the obtained product to stand; and vi) forming a hardshell gelatin capsule therefrom.

2 Claims, No Drawings

HARDSHELL GELATIN CAPSULE REDUCING THE STATIC ELECTRICITY AND ENHANCING THE LUBRICATION OF FILM

This is a continuation-in-part of U.S. Ser. No. 09/756,708, field Jan. 10, 2001 and now abandoned.

BACKGROUND OF THE INVENTION

The present invention relates to hardshell gelatin capsules prepared by the addition of mixed solution of diacetylated monoglycerides, sodium lauryl sulfate and colloidal silicon dioxide during the gelatin film formulation in order to reduce the static electricity and to enhance the lubrication of film, with maintaining the constant film distribution in capsule and its preparation method thereof.

Hardshell gelatin capsule has been conventionally manufactured by following processes; i) dipping, molding and drying gelatin film according to the mold pin dipping method in the capsule manufacturing machine, ii) stripping off the gelatin film from mold pin and cutting off, iii) joining the film of cap and the film of body to be one set of capsule at the Joiner Block made by metal substance, and iv) finally, ejecting out prepared gelatin capsule by Ejector Rod.

In the course of joining the film of cap and the film of body, static electricity sometimes generates and induces low film flexibility, which causes the bad joint or telescope, one of fatal badness in capsule manufacturing industry. Further, the bad joint causes the separation of cap and body during the transportation and the badness in imprinting process as well as the badness in filling the capsule.

To solve the above problems, it has been conventionally used to add glycerine or sorbitol to the gelatin solution to maintain the flexibility of capsule film. However, such plasticizer induces the delay of drying at the drying step after molding step in the capsule manufacturing machine. Further, it also induces some drawbacks such as deformation and contraction of the film of cap or body at the time of long term storage. Therefore, those plasticizers increase the unstability of gelatin capsules with time.

In Japanese laying open patent No. 6-157916, it is disclosed that 3~10 wt % of glycerine fatty acid ester is added to the gelatin solution during the manufacturing the gelatin capsule film. Further, as an example of glycerine fatty acid ester, diacetylated monoglycerides was disclosed. However, the purpose for using glycerine fatty acid ester in gelatin solution is to maintain the elasticity of gelatin film at the time of filling hygroscopic drug as internal ingredient, because such preparation protects the absorption of moisture from the gelatin capsule film to the hygroscopic internal drug. Further, such preparation protects the leakage of internal drug at the time of external impact to the capsule.

To solve the above problems, the inventors design the reformation of gelatin film formulation in order to reduce the static electricity and to enhance the lubrication of film, with maintaining the constant film distribution in capsule. For this purpose, diacetylated monoglyceride is employed together with sodium lauryl sulfate which emulsifies the mixed gelatin solution by reducing the surface tension between water phase and oil phase.

On the other hand, colloidal silicon dioxide is also employed in order to maintain the constant film distribution in capsule, by reducing the entasis formulation caused by flow of gelatin by using diacetylated monoglycerides.

Such ingredients, diacetylated monoglycerides and sodium lauryl sulfate are recorded in NF. In this reference, diacetylated monoglycerides is described in various usage, for example, anti-dusting agent, deforming agent, lubricant, stabilizer, plasticizer or release agent. However, in this invention, diacetylated monoglycerides is used as an agent for reducing static electricity.

Further, colloidal silicon dioxide also has a role of caking agent to avoid the flow of gelatin from mold pin in order to maintain the constant film distribution in capsule.

SUMMARY OF THE INVENTION

The object of the present invention is to provide a process for preparing hardshell gelatin capsule reducing the static electricity and enhancing the lubrication of film having good film distribution in capsule comprising the steps of: i) preparing an emulsion containing 0.4~0.8 part by weight of diacetylated monoglycerides, 0.05~0.1 part by weight of sodium lauryl sulfate, and 0.005~0.01 part by weight of colloidal silicon dioxide; ii) adding the emulsion to gelatin solution containing 100 part by weight of gelatin; iii) mixing and homogenizing the resulting solution; iv) adjusting viscosity of mixture; v) allowing the obtained product to stand; and vi) forming a hardshell gelatin capsule therefrom.

In particular, diacetylated monoglycerides is in the phase of transparent liquid and the HLB value of sodium lauryl sulfate as anion surfactant is 38~42.

Further, colloidal silicon dioxide is used as a caking agent.

DETAILED DESCRIPTION OF THE INVENTION

Followings are steps and methods for preparing a hardshell gelatin capsule reducing the static electricity and enhancing the lubrication of film of the present invention.

In the first step, diacetylated monoglycerides is dissolved with purified water together with sodium lauryl sulfate as surfactant. Also, colloidal silicon dioxide is added as caking agent. If the addition of colloidal silicon dioxide is less than 0.005 part by weight, it cannot control the flow of gelatin from mold pin. On the other hand, if the addition of colloidal silicon dioxide is more than 0.01 part by weight, it makes the top part of capsule too much thick.

Said mixed solution is stirred and homogenized to become an emulsion in 2,700~3,300 rpm of stirring velocity for about 2 hours.

Said emulsion is added to gelatin solution. Said gelatin mixed solution has been stirred until the completion of dissolving. Then, coloring agent, such as, titanium dioxide is added to completely dissolved gelatin solution and it is laid on standing after adjusting viscosity. After complete removal of bubble, the film is formed into the capsule in the capsule manufacturing machine according to conventional method.

In case that the mixed contents of diacetylated monoglycerides and sodium lauryl sulfate is less than 0.3 wt part, the activity for reducing the static electricity and for enhancing the lubrication of film is not satisfactory. On the other hand, in case that the mixed contents of diacetylated monoglycerides and sodium lauryl sulfate is more than 1.0 wt part, the surface of gelatin capsule becomes uneven.

Diacetylated monoglycerides and sodium lauryl sulfate used in this invention have the properties described in The United States Pharmacopeia 24/The National Formulary 19. Further, gelatin has also the properties described in USP 24/NF 19.

The present invention will be more specifically explained by the following examples. However, it should be understood that the examples are intended to illustrate but not in any manner to limit the scope of the present invention.

REFERENCE EXAMPLE

In the first step, diacetylated monoglycerides is dissolved with purified water together with sodium lauryl sulfate as surfactant. In detail, 12.5 L of purified water about 60° C. is measured and laid on a vessel. With stirring the water at about 3,000 rpm, 0.5 Kg of sodium lauryl sulfate is added. Then, 4.0 Kg of diacetylated monoglycerides is added with 0.025 Kg of colloidal silicon dioxide and stirred for 2 hours in order to make emulsion.

Next, prepared emulsion of previous step is added to the gelatin solution (conc. 31.25 w/v %) to be in the proportion of 0.8 Kg of diacetylated monoglycerides to 100 Kg of gelatin. Said gelatin mixed solution is stirred at 60 rpm for about 2 hours until the completion of solubilization. Then, coloring agent, such as, titanium dioxide or other pigment is added to completely dissolved gelatin solution and it is laid on standing for more than 4 hours after adjusting viscosity. After complete removal of bubble, the film is formed into the capsule in the capsule manufacturing machine according to conventional method. Finally, hardshell gelatin capsule of the present invention is obtained.

The hardshell gelatin capsule used for control group is manufactured by conventional method using only gelatin solution without adding an emulsion containing diacetylated monoglycerides and sodium lauryl sulfate.

Example 1
Static Electricity Occurrence Test

To measure the static electricity occurrence, the inventor has prepared a cylinder type of drum (Φ: 445 mm) having a rectangular shape of outlet (210 mm×230 mm) on the side bottom. On the opposite side, 700 mm of scale is attached.

The measuring method is as follows. After sealing the outlet, about 90,000 capsules are laid on the drum. This drum is lifted on 1,000 mm height support, and the outlet is opened for dropping capsules down. The static electricity is measured by the machine [Static V. Meter "STATIRON-M" made by Shisido Co., Ltd. Japan] at the 30 mm distance from the outlet.

Table 1 shows the result for static electricity occurrence test between the capsule manufactured by present invention method and the control capsule. As shown in Table 1, the occurrence of static electricity of present invented capsule is remarkably reduced.

TABLE 1

Comparison of occurrence of static electricity

|  | Present invented capsule | Control capsule |
|---|---|---|
| Static electricity occurrence | 3~4 | 7~8 |

Example 2
Lubrication Test

To measure the static electricity occurrence, the inventor has prepared a cylinder type of drum (Φ: 445 mm) having a rectangular shape of outlet (210 mm×230 mm) on the side bottom. On the opposite side, 700 mm of scale is attached.

The measuring method is as follows. After sealing the outlet, about 90,000 capsules are laid on the drum. This drum is lifted on 1,000 mm height support, and the outlet is opened for dropping capsules down. After the finish of dropping, the height of the capsule dropped is measured. The lower height means better lubrication of the capsule.

Table 2 shows the result for lubrication test (sliding test) between the capsule manufactured by present invention method and the control capsule. As shown in Table 2, the lubrication of present invented capsule is remarkably enhanced.

TABLE 2

Comparison of lubrication

|  | Present invented capsule | Control capsule |
|---|---|---|
| Sliding test | 19 cm | 26 cm |

Example 3
Filling Property & Quality Test

Table 3 shows the result of filling property test between the capsule manufactured by present invention method and the control capsule. As shown in Table 3, the filling property of present invented capsule is excellent and there is no observed defects of joint, such as bad joint and telescope in filling.

TABLE 3

Comparison of filling property

|  | Zanasi AZ-20 | Zanasi AZ-40 |
|---|---|---|
| Filling speed | 15,000 EA/hour | 35,000 EA/hour |
| Pressure | 20 cmHg | 25 cmHg |
| Filling Q'ty | 100,000 EA | 100,000 EA |

| Result |  | Present invented capsule | Control capsule |  | Present invented capsule | Control capsule |
|---|---|---|---|---|---|---|
|  | Water content | 14.0% | 14.0% | Water content | 13.5% | 13.5% |
|  | Joint defects | none | 12 EA | Joint defects | none | 20 EA |

Table 4 shows the result of quality test between the capsule manufactured by present invention method and the control capsule by measuring bad joint and telescope. As shown in Table 4, the quality of present invented capsule is remarkably enhanced by reducing the bad joint and telescope, which are sometimes observed in filling and capsule manufacturing process.

TABLE 4

Comparison of quality

|  | Present invented capsule |  | Control capsule |  |
|---|---|---|---|---|
| Speed of machine | 70,000 EA/hour |  | 70,000 EA/hour |  |
| Spec of capsule | Size: #1 |  | Size: #1 |  |
| Quantity | 4,500,000 caps |  | 4,500,000 caps |  |
| Result | Bad joint | Telescope | Bad joint | Telescope |
|  | 1 EA | none | 50 EA | 8 EA |

Example 4
Solubility & Disintegration Test

For solubility test, measuring method is carried out according to Japanese Pharmacopeia. 50 ml of purified water is inserted to 100 ml of flask. At 37±0.5° C., we measure the time required for completely dissolving hardshell capsule after separating Cap and Body. Each group of capsule is measured 5 times and the standard requirement is solubilized within 10 minutes for complete solution.

For disintegration test, measuring method is carried out according to Japanese Pharmacopeia. We measure the time required complete disintegration of hardshell capsule at 37±0.5° C. Each group of capsule is measured 5 times and the standard requirement is disintegrated within 20 minutes for complete disintegration.

Table 5 shows the result of solubility and disintegration test between the capsule manufactured by present invention method and the control capsule by measuring the time required.

As shown in Table 5, the solubility and disintegration property of present invented hardshell gelatin capsule is almost equal to the control capsule. Both of them meet the standard requirement in Japanese Pharmacopeia.

TABLE 5

Comparison of solubility and disintegration

|  | Present invented capsule | Control capsule |
| --- | --- | --- |
| Solubility (pH 6.0~7.0) | Avg. 3' 16"<br>Max. 3' 24"<br>Min. 3' 08" | Avg. 3' 10"<br>Max. 3' 20"<br>Min. 3' 00" |
| Disintegration (pH 6.0~7.0) | Avg. 12' 20"<br>Max. 12' 40"<br>Min. 12' 00" | Avg. 12' 13"<br>Max. 12' 35"<br>Min. 11' 50" |

As described above, the gelatin capsule of the present invention provides an efficient gelatin capsule reducing the static electricity and enhancing the lubrication of film. The addition of the mixture of diacetylated monoglycerides and sodium lauryl sulfate to gelatin solution enables the present invented capsule to have such advantageous property. Further, the present invented capsule enables the increase of productivity of capsule by improving each manufacturing steps; transfer step of capsule, printing step of capsule, and filling step of capsule.

What is claimed is:

1. A process for preparing hardshell gelatin capsules while reducing static electricity and enhancing the lubrication of gelatin films distributed therein, which process comprises the steps:

i) preparing an emulsion containing 0.4 to 0.8 part by weight of one or more diacetylated monoglycerides, 0.05 to 0.1 part by weight of sodium lauryl sulfate and 0.005 to 0.01 part by weight of colloidal silicon dioxide as a caking agent;

ii) adding the emulsion to a gelatin solution containing 100 parts by weight of gelatin;

iii) mixing and homogenizing the product of step ii);

iv) adjusting the viscosity of the mixture of step iii);

v) allowing the product of step iii) to stand; and vi) forming a hardshell gelatin capsule therefrom.

2. The process of claim 1 wherein the diacetylated monoglycerides are transparent liquids and the HLB value of the sodium lauryl sulfate is between 38 and 42.

* * * * *